United States Patent
Wagner et al.

[11] Patent Number: 5,994,551
[45] Date of Patent: Nov. 30, 1999

[54] 1-HETEROCYCLYL METHYL-2-NITRO-OR-CYANOIMINIDAZOLINE SALTS, PROCESS FOR THEIR PREPARATION, PESTICIDAL COMPOSITION CONTAINING THEM, AND PESTICIDAL METHOD OF USING THEM

[75] Inventors: Klaus Wagner, Köln; Christoph Erdelen, Leichlingen, both of Germany

[73] Assignee: Bayer Aktiengesenllschaft, Leverkusen, Germany

[21] Appl. No.: 09/117,767

[22] PCT Filed: Feb. 3, 1997

[86] PCT No.: PCT/EP97/00475

§ 371 Date: Aug. 5, 1998

§ 102(e) Date: Aug. 5, 1998

[87] PCT Pub. No.: WO97/30043

PCT Pub. Date: Aug. 21, 1997

[30] Foreign Application Priority Data

Feb. 14, 1996 [DE] Germany .................. 196 05 400

[51] Int. Cl.⁶ .................. C07D 401/06; C07D 417/06; A01N 43/50
[52] U.S. Cl. .................. 546/274.7; 514/341; 514/392; 546/273.1; 548/202; 548/203; 548/205
[58] Field of Search .................. 546/273.1, 274.7; 548/202, 203, 205; 514/392, 341

[56] References Cited

U.S. PATENT DOCUMENTS

| | | | |
|---|---|---|---|
| 4,803,277 | 2/1989 | Shiokawa et al. | 514/332 |
| 4,845,106 | 7/1989 | Shiokawa et al. | 514/342 |
| 4,849,432 | 7/1989 | Shiokawa et al. | 514/341 |
| 4,876,263 | 10/1989 | Shiokawa et al. | 514/338 |
| 4,914,113 | 4/1990 | Shiokawa et al. | 514/333 |
| 4,960,780 | 10/1990 | Shiokawa et al. | 514/300 |
| 5,036,082 | 7/1991 | Shiokawa et al. | 514/338 |
| 5,461,167 | 10/1995 | Shiokawa et al. | 548/202 |

FOREIGN PATENT DOCUMENTS

| | | |
|---|---|---|
| 192060 | 8/1986 | European Pat. Off. . |
| 235725 | 9/1987 | European Pat. Off. . |
| 259738 | 3/1988 | European Pat. Off. . |
| 315826 | 5/1989 | European Pat. Off. . |

*Primary Examiner*—Floyd D. Higel
*Attorney, Agent, or Firm*—Sprung Kramer Schaefer & Briscoe

[57] ABSTRACT

The present invention relates to salts of imidazoline derivatives of the formula I

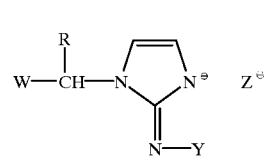

(I)

in which
R represents hydrogen or alkyl,
Y represents nitro or cyano,
W represents an optionally substituted 5- or 6-membered heterocyclic radical and
Z represents one equivalent of an alkali metal or alkaline earth metal or of an [NR¹R²R³R⁴] grouping, wherein R¹, R², R³ and R⁴ are identical or different and represent hydrogen, alkyl, optionally substituted cycloalkyl or optionally substituted benzyl, and to their preparation and their use as agents for controlling pests.

4 Claims, No Drawings

1-HETEROCYCLYL METHYL-2-NITRO-OR-CYANOIMINIDAZOLINE SALTS, PROCESS FOR THEIR PREPARATION, PESTICIDAL COMPOSITION CONTAINING THEM, AND PESTICIDAL METHOD OF USING THEM

This application is a 371 of PCT/EP97/00475, which was filed on Feb. 3, 1997.

The present invention relates to novel salts of imidazoline derivatives, a process for their preparation and their use for controlling animal pests.

It is already known that certain alkylated imidazoline derivatives, such as, for example, 1-(2-chloropyrimidin-5-yl)-3-methyl-2-nitroiminoimidazoline, have insecticidal properties (cf., for example, EP-A 0 315 826). However, the activity and range of action of these compounds is not always completely satisfactory, especially if low amounts are used and at low concentrations.

Novel salts of imidazoline derivatives of the formula I

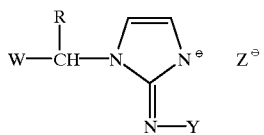

(I)

in which

R represents hydrogen or alkyl,

Y represents nitro or cyano,

W represents an optionally substituted 5- or 6-membered heterocyclic radical and Z represents one equivalent of an alkali metal or alkaline earth metal or of an $[NR^1R^2R^3R^4]$ grouping, wherein $R^1$, $R^2$, $R^3$ and $R^4$ are identical or different and represent hydrogen, alkyl, optionally substituted cycloalkyl or optionally substituted benzyl, have been found.

It has furthermore been found that the salts of the imidazoline derivatives of the formula (I) are obtained by a process in which imidazolines of the formula (II)

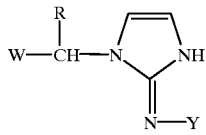

(II)

in which

R, Y and W have the abovementioned meaning, are reacted with hydroxides of the formula (III)

Z—OH (III)

in which

Z has the abovementioned meaning, in the presence of a diluent.

Finally, it has been found that the novel salts of imidazoline derivatives of the formula (I) have highly pronounced biological properties, and are suitable above all for controlling animal pests, in particular insects, arachnids and nematodes, which occur in agriculture, in forestry, in the preservation of stored products and materials and in the hygiene sector.

Formula (I) provides a general definition of the salts according to the invention of imidazoline derivatives.

Preferred substituents and ranges of the radicals listed in the formulae mentioned above and below are explained in the following.

R preferably represents hydrogen or $C_1$–$C_4$-alkyl.

Y preferably represents nitro or cyano.

W preferably represents a 5- or 6-membered heterocyclic radical which contains 1 or 2 identical or different heteroatoms, such as, preferably, nitrogen, oxygen or sulfur atoms, and is optionally substituted once to three times in an identical or different manner, substituents which may be mentioned being: halogen, $C_1$–$C_4$-alkyl, $C_1$–$C_4$-alkoxy, $C_1$–$C_4$-halogenoalkyl, $C_1$–$C_4$-halogenoalkoxy, $C_1$–$C_4$-alkylthio, $C_1$–$C_4$-alkylsulfinyl, $C_1$–$C_4$-alkylsulfonyl, $C_1$–$C_4$-halogenoalkylthio, $C_1$–$C_4$-halogenoalkylsulfinyl, $C_1$–$C_4$-halogenoalkylsulfonyl or $C_1$–$C_2$-alkenyl.

Z preferably represents in each case one equivalent of lithium, sodium, potassium, rubidium, cesium, magnesium, calcium, ammonium, $C_1$–$C_4$-alkylammonium, di-($C_1$–$C_4$-alkyl)-ammonium, tri-($C_1$–$C_4$-alkyl)-ammonium, tetra-($C_1$–$C_4$-alkyl)-ammonium, $C_5$- or $C_6$-cycloalkyl-ammonium or di-($C_1$–$C_2$-alkyl)-benzyl-anmmonium.

R particularly preferably represents hydrogen or methyl.

Y particularly preferably represents nitro or cyano.

W particularly preferably represents in each case optionally substituted pyridyl, thiazolyl, oxazolyl, isothiazolyl or isoxazolyl, substituents which may be mentioned being: fluorine, chlorine, bromine, methyl, ethyl, trifluoromethyl, methoxy, trifluoromethoxy, methylthio, methylsulfinyl or methylsulfonyl.

Z particularly preferably in each case represents one equivalent of lithium, sodium, potassium, rubidium, cesium, magnesium, calcium, ammonium, methylammonium, dimethylammonium, trimethylammonium, tetramethylammonium, tetraethylammonium, tetra-n-propyl-ammonium, tetra-n-butylammonium or dimethylbenzyl-ammonium.

Preferred compounds according to the invention are substances of the formulae (IA) to (ID):

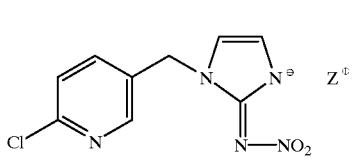

(IA)

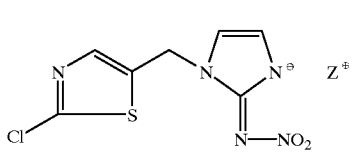

(IB)

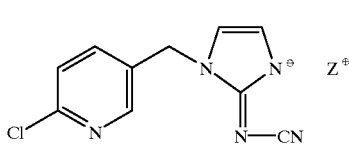

(IC)

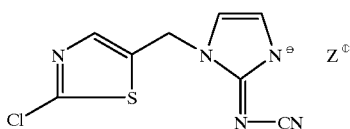

(ID)

in which

Z represents the abovementioned general, preferred and particularly preferred meanings.

The radical definitions and explanations listed above, whether general or in ranges of preference, apply correspondingly to the end products and to the starting products and intermediates. These radical definitions can be combined with one another as desired, therefore including combinations between the respective ranges of preference.

Compounds of the formula (I) which are preferred according to the invention are those in which a combination of the meanings listed above as preferred (preferably) is present.

Compounds of the formula (I) which are particularly preferred according to the invention are those in which a combination of the meanings listed above as particularly preferred is present.

In the definitions of radicals listed above and below, hydrocarbon radicals, such as alkyl or alkenyl—including in combination with heteroatoms, such as alkoxy or alkylthio—are, where possible, in each case straight-chain or branched.

If, for example, 3H-1-(2-chloropyridin-5-yl)-2-nitroiminoimidazoline and lithium hydroxide are used as starting substances, the course of the reaction in the process according to the invention can be represented by the following equation:

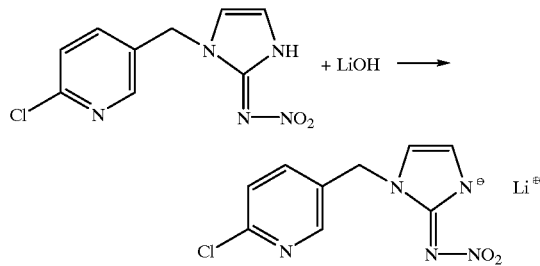

The imidazolines of the formula (II) to be used as starting substances in the process according to the invention are known (cf., for example, EP-A 0 259 738 and EP-A 0 315 826), and/or they can be prepared by known methods (cf., for example, the abovementioned literature references).

The hydroxides of the formula (III) furthermore to be used as starting substances in the process according to the invention are generally known compounds.

The process according to the invention is carried out in the presence of a diluent. Diluents which can preferably be used are water and organic/aqueous systems, it being possible for all the customary water-miscible organic solvents to be employed. Examples which may be mentioned are ketones, such as acetone, methyl ethyl ketone or methyl isobutyl ketone; nitrites, such as acetonitrile or propionitrile, and alcohols, such as methanol or ethanol.

The reaction temperatures can be varied within a substantial range in the process according to the invention. The reaction is in general carried out at temperatures between 0 and 100° C., preferably between 0 and 60° C.

In carrying out the process according to the invention, in general 0.9 to 1.5 mol, preferably 0.95 to 1.2 mol or molar equivalents of a hydroxide of the formula (III) are employed per mol of imidazoline of the formula (II).

Working up and isolation of the end products are carried out in the generally known manner.

In some cases, it proves advantageous to employ the compounds of the formula (III) in the form of their alcoholates.

The active compounds are suitable for controlling animal pests, in particular insects, arachnids and nematodes, which are encountered in agriculture, in forestry, in the protection of stored products and of materials, and in the hygiene field, and have good plant tolerance and favourable toxicity to warm-blooded animals. They can preferably be used as plant protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Spodoptera litura,* Spodoptera spp., *Trichoplusia ni, Carpocapsa pomonella,*

Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderrna spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, Acarus siro, Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include, for example, Pratylenchus spp., *Radopholus similis, Ditylenchus dipsaci, Tylenchulus semipenetrans,* Heterodera spp., Globodera spp., Meloidogyne spp., Aphelenchoides spp., Longidorus spp., Xiphinema spp. and Trichodorus spp.

The compounds of the formula (I) according to the invention are distinguished in particular by a high insecticidal activity.

They can be employed particularly successfully to control plant-damaging insects, such as, for example, against the larvae of the mustard beetle (*Phaedon cochlaeriae*), the caterpillars of the cabbage moth (*Plutella maculipennis*), the green rice cicada (*Nephotettix cinctriceps*), the caterpillars of the owlet moth (*Spodoptera frugiperda*) or peach leaf aphids (*Mycus persicae*).

The active compounds can be converted into the customary formulations, such as solutions, emulsions, wettable powders, suspensions, powders, dusts, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulfoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates as well as albumen hydrolysis products; as dispersing agents there are suitable: for example lignin sulfite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fumgicides, growth regulating substances or herbicides. The insecticides include, for example, phosphates, carbamates, carboxylates, chlorinated hydrocarbons, phenylureas, substances produced by microorganisms and the like.

Particularly suitable mixing partners are, for example, the following:
Fungicides:
2-aminobutane; 2-anilino-4-methyl-6-cyclopropyl-pyrimidine;2',6'-dibromo-2-methyl-4'-trifluoromethoxy-4'-trifluoro-methyl-1,3-thiazole-5-carboxanilide; 2,6-dichloro-N-(4-trifluoromethylbenzvl)benzamide;(E)-2-methoxyimino-N-methyl-2-(2-phenoxyphenyl)-acetamide; 8-hydroxyquinoline sulfate; methyl (E)-2-{2-[6-(2-cyanophenoxy)-pyrimidin-4-yloxy]-phenyl}-3- methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulfide, captafol, captan, carbendazim, carboxin, quinomethionate, chioroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminum, fthalide, fuberidazole, furalaxyl, fuirmecyclox, guazatine, hexachlorobenzene, hexaconazole, hymexazole, imazalil, imibenconazole, iminoctadine, iprobenfos (IBP), iprodione, isoprothiolane, kasugamycin, copper formulations such as: copper hydroxide, copper naphthenate, copper oxychloride, copper sulfate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulfur and sulfur formulations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bacteincides:

bronopol, dichlorophen, nitrapyrin, nickel dimethyldithiocarbamate, kasugamycin, octhilinone, furan-carboxylic acid, oxytetracycline, probenazole, streptomycin, tecloftalam, copper sulfate and other copper formulations.

Insecticides/acanicides/nematicides abamectin, AC 303 630, acephate, acrinathrin, alanycarb, aldicarb, alphamethrin, amitraz, avermectin, AZ 60541, azadirachtin, azinphos A, azinphos M, azocyclotin, *Bacillus thuringiensis*, bendiocarb, benfuracarb, bensultap, betacyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfen valerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, Iubfenprox, fiirathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyradaphenthion, pyresmethrin, pyrethrim, pyridaben, pyrimidifen, pyriproxifen, quinalphos,

RH 5992, salithion, sebufos, silafluofen, sulfotep, sulprofos, tebufenozide, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

A mixture with other known active compounds, such as herbicides, or with fertilizers and growth regulators, is also possible.

The active compounds according to the invention can fuirthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an outstanding residual action on wood and clay and by a good stability to alkali on limed substrates.

The active compounds according to the invention not only act against plant pests, hygiene pests and pests of stored products, but also in the veterinary sector against animal parasites (ectoparasites), such as hard ticks, soft ticks, mange mites, harvest mites, flies (biting and licking), parasitic fly larvae, lice, hair lice, feather lice and fleas. These parasites include:

From the order of the Anoplurida, for example, Haematopinus spp., Linognathus spp., Pediculus spp., Phtirus spp. and Solenopotes spp.

From the order of the Mallophagida and the suborders Amblycerina and Ischnocerina, for example, Trimenopon spp., Menopon spp., Trinoton spp., Bovicola spp., Wemeckiella spp., Lepikentron spp., Damalina spp., Trichodectes spp. and Felicola spp.

From the order of the Diptera and the suborders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybromitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanica* and Supella spp.

From the subclass of the Acaria (Acarida) and the orders of the Meta- and Mesostigmata, for example, Argas spp., Ornithodorus spp., Otobius spp., Ixodes spp., Amblyomma spp., Boophilus spp., Dermacentor spp., Haemophysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

The active compounds according to the invention of the formula (I) are also suitable for combating arthropods which infest agricultural productive livestock such as, for example, cattle, sheep, goats, horses, pigs, donkeys, camels, buffalo, rabbits, chickens, turkeys, ducks, geese and bees, other pets, such as, for example, dogs, cats, cage birds and aquarium fish, and also so-called test animals, such as, for example, hamsters, guinea pigs, rats and mice. By combating these arthropods cases of death and reductions in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boli, the feed-through process and suppositories, by parenteral administration, such as, for example, by injections (intra-muscular, subcutaneous, intravenous, intraperitoneal etc.), implants, by nasal administration, by dermal use in the form, for example, of dipping or bathing, spraying, pouring on and spotting on, washing and powdering, and also with the aid of moulded articles containing the active compound, such as collars, ear tags, tail tags, limb bands, halters, marking devices, etc.

When used for livestock, poultry, pets and the like, the active compounds of the formula (I) can be used as formulations (for example powders, emulsions, free-flowing mixtures), which comprise the active compounds in an amount of 1 to 80% by weight, directly or after 100- to 10,000-fold dilution, or they can be used as a chemical bath.

It has furthermore been found that the compounds of the formula (I) according to the invention have a potent insecticidal action against insects which destroy industrial materials.

The following insects may be mentioned as examples and as preferred—but without a limitation:

beetles, such as

*Hylotrupes bajulus, Chlorophorus pilosis, anobium punctatum, Xestobium rufovillosum, Ptilinus pecticornis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis*; Xyleborus spec. Tryptodendron spec. *Apate monachus, Bostrychus capucins, Heterobostrychus brunneus*, Sinoxylon spec. and *Dinoderus minutus.*

Hymenopterans, such as

*Sirex juvencus, Urocerus gigas, Urocerus gigas taignus* and *Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as Lepisma saccarina.

Industrial materials in the present connection are to be understood as meaning non-living materials, such as, preferably, plastics, adhesives, sizes, papers and cards, leather, wood and processed wood products and paints.

The material to be preserved against attack by insects is especially preferably wood and processed wood products.

Wood and processed wood products which are to be preserved by the agent according to the invention or mixtures comprising this are to be understood as meaning, for example: building timber, wooden beams, railway sleepers, bridge components, boat jetties, wooden vehicles, crates, pallets, containers, telegraph poles, wood paneling, wooden windows and doors, plywood, chipboard, joinery or wooden products which are used quite generally in housebuilding or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water-repellent, if appropriate siccatives and UV stabilizers and if appropriate dyestuffs and pigments, as well as other processing auxiliaries.

The insecticidal compositions or concentrates used for preservation of wood and derived timber products comprise the active compound according to the invention in a concentration of 0.0001 to 95% by weight, in particular 0.001 to 60% by weight.

The amount of the compositions or concentrates which are employed depends on the nature and the occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

The solvent and/or diluent used is an organic chemical solvent or solvent mixture and/or an oily or oil-like organic chemical solvent or solvent mixture of low volatility and/or a polar organic chemical solvent or solvent mixture and/or water and if appropriate an emulsifier and/or wetting agent.

Organic chemical solvents which are preferably employed are oily or oil-like solvents having an evaporation number above 35 and a flash point above 30° C., preferably above 45° C. Corresponding mineral oils or aromatic fractions thereof or solvent mixtures containing mineral oil, preferably test benzine, petroleum and/or alkylbenzene, are used as such water-insoluble, oily and oil-like solvents of low volatility.

Mineral oils having a boiling range from 170 to 220° C., test benzine having a boiling range from 170 to 220° C., spindle oil having a boiling range from 250 to 350° C., petroleum or aromatics having a boiling range from 160 to 280° C., terpentine oil and the like are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility and having an evaporation number above 35 and a flash point above 30° C., preferably above 45° C., can be replaced in part by organic chemical solvents of high or medium volatility, providing that the solvent mixture likewise has an evaporation number above 35 and a flash point above 30° C., preferably above 45° C., and that the insecticide/fungicide mixture is soluble or emulsifiable in this solvent mixture.

According to a preferred embodiment, some of the organic chemical solvent or solvent mixture or an aliphatic polar organic chemical solvent or solvent mixture is replaced. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are water-dilutable and/or soluble or dispersible or emulsifiable in the organic chemical solvents employed and are known per se, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable and/or drying oils and/or physically drying binders based on a natural and/or synthetic resin.

The synthetic resin used as binder can be employed in the form of an emulsion, dispersion or solution. Bitumen or bituminous substances can also be used as binders in an amount of up to 10% by weight. In addition, dyestuffs, pigments, water-repellent agents, odor correctants and inhibitors or anticorrosion agents and the like which are known per se can be employed.

According to the invention, the composition or concentrate preferably comprises at least one alkyd resin or modified alkyd resin and/or one drying vegetable oil as organic chemical binder. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulfonic acid esters.

Fixing agents are based chemically on polyvinyl alkyl ethers, such as, for example, polyvinyl methyl ether, or ketones, such as benzophenone or ethylenebenzophenone.

A possible solvent or diluent is, in particular, also water, if appropriate mixed with one or more of the abovementioned organic chemical solvents or diluents, emulsifiers and dispersing agents.

Particularly effective wood preservation is achieved by impregnation processes on a large industrial scale, for example vacuum, double vacuum or pressure processes.

The ready-to-use compositions can also comprise other insecticides, if appopriate, and also comprise one or more fungicides, if appropriate.

Possible additional mixing partners are, preferably, the insecticides and fungicides mentioned in WO 94/29 268. The compounds mentioned in this document are an explicit constituent of the present Application.

Especially preferred mixing partners can be insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octylisothiazolin-3-one and 4,5-dichloro-N-octylisothiazolin-3-one.

The preparation and the use of the active compounds according to the invention can be seen from the following examples.

PREPARATION EXAMPLES

Example 1

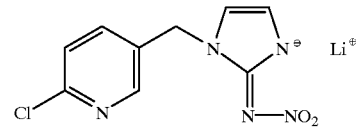

2.52 g (0.01 mol) of 3H-1-(2-chloropyridin-5-yl)-2-nitroimino-imidazoline and 0.24 g (0.01 mol) of lithium hydroxide are dissolved in 30 ml of water and the solution is stirred at room temperature for a short time. The reaction solution is filtered and the filtrate is concentrated in vacuo. The residue is dried in vacuo over phosphorus pentoxide.

2.43 g (93% of theory) of the lithium salt of 3H-1-(2-chloropyridin-5-yl)-2-nitroimino-imidazoline are obtained.

MS spectrum (by the FAB method)*: MH$^+$=260.

[* FAB: fast atom bombardment]

The following compounds of the formula (I) are obtained analogously or in accordance with the general instructions for the preparation:

TABLE 1
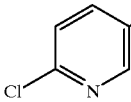
(I)
| Ex. No. | R | Y | W | Z | MS Data (FAB Method) |
|---|---|---|---|---|---|
| 2 | H | NO$_2$ | 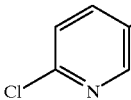 | Na | MH+ = 276 |
| 3 | H | NO$_2$ | 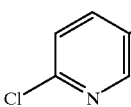 | K | MH+ = 292 |
| 4 | H | NO$_2$ | 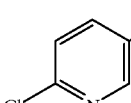 | Cs | MH+ = 386 |
| 5 | H | NO$_2$ | 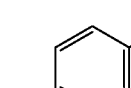 | Rb | MH+ = 338 |
| 6 | H | NO$_2$ | 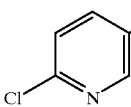 | N(CH$_3$)$_4$ | [M—N(CH$_3$)$_4$]$^\ominus$ = 252 |
| 7 | H | NO$_2$ | 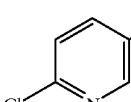 | Ca | [M—Ca]$^\ominus$ = 252 |
| 8 | H | NO$_2$ | 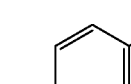 | N(C$_3$H$_7$-n)$_4$ | [M—N(C$_3$H$_7$-n)$_4$]$^\ominus$ = 252 |
| 9 | H | NO$_2$ | 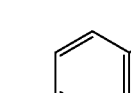 | N(C$_2$H$_5$)$_4$ | [M—N(C$_2$H$_5$)$_4$]$^\ominus$ = 252 |
| 10 | H | NO$_2$ |  | N(C$_4$H$_9$-n)$_4$ | [M—N(C$_4$H$_9$-n)$_4$]$^\ominus$ = 252 |

USE EXAMPLES

The compound shown below is employed as the comparison substance in the following use examples:

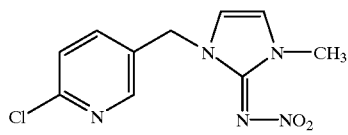

Compound (A) known from EP-A 0 315 826
1-(2-Chloropyridin-5-yl)-3-methyl-2-nitroimino-imidazoline

Example A

Phaedon larvae test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration. Cabbage leaves (*Brassica oleracea*) are treated by being dipped into the preparation of the active compound of the desired concentration and are infested with mustard beetle larvae (*Phaedon cochleariae*), as long as the leaves are still moist. After the specified period of time, the destruction in % is determined. 100% means that all the beetle larvae have been killed; 0% means that none of the beetle larvae has been killed.

In this test, at an active compound concentration of, for example, 0.01%, for example, the compound according to Preparation Example 1 caused a destruction of 90% and the compounds of Preparation Examples 2, 3, 4 and 5 caused a destruction of 100%, in each case after 7 days, while the known compound (A) showed a destruction of only 10%.

Example B

Plutella test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration. Cabbage leaves (*Brassica oleracea*) are treated by being dipped into the preparation of active compound of the desired concentration and are infested with caterpillars of the diamond-back moth (*Plutella maculipennis*) while the leaves are still moist. After the specified period of time, the destruction in % is determined. 100% means that all the caterpillars have been killed; 0% means that none of the caterpillars has been killed.

In this test, at an active compound concentration of, for example, 0.1%, for example, the compounds according to Preparation Examples 2, 3, 4 and 5 caused a destruction of 100% and the compound of Preparation Example 6 caused a destruction of 85%, in each case after 7 days, while the known compound (A) showed a destruction of only 25%.

Example C

*Spodoptea frugiperda* test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration. Cabbage leaves (*Brassica oleracea*) are treated by being dipped into the preparation of active compound of the desired concentration and are infested with caterpillars of the owlet moth (*Spodoptera frugiperda*), as long as the leaves are still moist. After the specified period of time, the destruction in % is determined. 100% means that all the caterpillars have been killed; 0% means that none of the caterpillars has been killed.

In this test, for example, the compounds according to Preparation Examples 1, 2, 3, 4, 5 and 6 caused a destruction of 100% after 7 days at an active compound concentration of, for example, 0.1%, while the known compound (A) showed a destruction of only 50%.

Example D

Nephotettix test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration. Rice seedlings (*Oryza sativa*) are treated by being dipped into the preparation of active compound of the desired concentration and are infested with larvae of the green rice cicada (*Nephotettix cincticepts*), as long as the seedlings are still moist. After the specified period of time, the destruction in % is determined. 100% means that all the cicadas have been killed; 0% means that none of the cicadas has been killed.

In this test, for example, the compounds according to Preparation Examples 1, 2, 3, 4, 5 and 6 caused a destruction of 100% after 6 days at an active compound concentration of, for example, 0.001%, while the known compound (A) showed a destruction of only 50%.

Example E

*Myzus penicae*—sachet test
Solvent: Water, depending on the solubility, acetone A 0.1% stock solution in the appropriate solvent was prepared for each of the active compounds. The stock solution was diluted to the appropriate test concentration with a 15% strength solution of sucrose in water.

The particular active compound solution was pipetted into a synthetic double membrane (=sachet) of parafilm. The double membrane is drawn over a vessel which holds 15 adult peach aphids (*Mycus persicae*). In this test method, the aphids take in the active compound exclusively orally.

After the specified period of time, the destruction in percent is determined at various concentrations. The LC 50 values are calculated by means of Probit analysis. The LC 50 value indicates the concentration at which 50% of the animals employed are killed. The lower the LC 50 value, the better the action of the preparation.

In this test, for example, LC 50 values of between 0.006 ppm and 0.048 ppm result for the compounds of Preparation Examples 1, 2, 3, 4, 5 and 6 after 2 days, while the known compound (A) has an LC 50 value of 0.15.

TABLE E (plant-damaging insects)
*Myzus persicae*-Sachettest

| Active compound | LC 50 value after 2 d in ppm |
|---|---|
| (A) (known) | 0,15 |
| Li⊕ (1) | 0,006 |
| Na⊕ (2) | 0,017 |
| K⊕ (3) | 0,048 |
| Cs⊕ (4) | 0,023 |
| Rb⊕ (5) | 0,014 |
| [N(CH₃)₄]⊕ (6) | 0,023 |

We claim:

1. A compound of the formula (I):

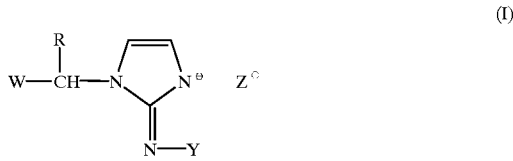

in which

R represents hydrogen or alkyl,

Y represents nitro or cyano,

W represents an unsubstituted or substituted 5- or 6-membered heterocyclic radical, and Z represents one equivalent of an alkali metal or alkaline earth metal other than sodium or of an [NR$^1$R$^2$R$^3$R$^4$] grouping, wherein
R$^1$, R$^2$, R$^3$, and R$^4$ are identical or different and represent hydrogen, alkyl, unsubstituted or substituted cycloalkyl or unsubstituted or substituted benzyl.

2. Process for the preparation of a compound of the formula (I) according to claim 1, said process comprising reacting a compound of the formula (II):

in which

R represents hydrogen or alkyl,

Y represents nitro or cyano, and

W represents an unsubstituted or substituted 5- or 6-membered heterocyclic radical, with a hydroxide of the formula (III):

in which

Z represents one equivalent of an alkali metal or alkaline earth metal other than sodium or of an [NR$^1$R$^2$R$^3$R$^4$] grouping, wherein
R$^1$, R$^2$, R$^3$, and R$^4$ are identical or different and represent hydrogen, alkyl, unsubstituted or substituted cycloalkyl or unsubstituted or substituted benzyl; in the presence of a diluent.

3. A pesticidal composition comprising a pesticidally effective amount of a compound according to claim 1 and a diluent.

4. A method of controlling pests comprising applying to pests or their environment a pesticidally effective amount of a compound of the formula (I):

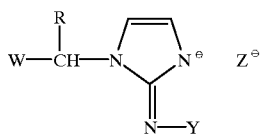 (I)

in which
R represents hydrogen or alkyl,
Y represents nitro or cyano,
W represents an unsubstituted or substituted 5- or 6-membered heterocyclic radical, and
Z represents one equivalent of an alkali metal or alkaline earth metal other than sodium or of an [NR$^1$R$^2$R$^3$R$^4$] grouping wherein
R$^1$, R$^2$, R$^3$ and R$^4$ are identical or different and represent hydrogen, alkyl, unsubstituted or substituted cycloalkyl or unsubstituted or substituted benzyl.

* * * * *